US007378554B2

(12) United States Patent
Hobbs et al.

(10) Patent No.: US 7,378,554 B2
(45) Date of Patent: May 27, 2008

(54) RING ALKYLATION OF ANILINE OR AN ANILINE DERIVATIVE USING IONIC LIQUID CATALYSTS

(75) Inventors: Steven J. Hobbs, Wolcott, CT (US); Venkatramanan K. Madabusi, Naugatuck, CT (US); Jin-Yun Wang, Cheshire, CT (US); Joseph F. Steiber, Prospect, CT (US)

(73) Assignee: Chemtura Corporation, Middlebury, CT (US)

( * ) Notice: Subject to any disclaimer, the term of this patent is extended or adjusted under 35 U.S.C. 154(b) by 111 days.

(21) Appl. No.: 11/304,307

(22) Filed: Dec. 14, 2005

(65) Prior Publication Data

US 2007/0135656 A1 Jun. 14, 2007

(51) Int. Cl.
*C07C 209/60* (2006.01)
(52) U.S. Cl. ..................................................... 564/409
(58) Field of Classification Search ...................... None
See application file for complete search history.

(56) References Cited

U.S. PATENT DOCUMENTS

| | | | |
|---|---|---|---|
| 3,275,690 A | 9/1966 | Stroh et al. | |
| 4,740,620 A | 4/1988 | Dixon et al. | 564/409 |
| 4,780,278 A | 10/1988 | Bacskai et al. | 422/7 |
| 4,876,377 A | 10/1989 | Agrawal et al. | 558/416 |
| 5,081,302 A | 1/1992 | Bayer et al. | 504/409 |
| 5,994,602 A * | 11/1999 | Abdul-Sada et al. | 585/457 |
| 6,204,424 B1 | 3/2001 | Yadav et al. | 585/502 |

FOREIGN PATENT DOCUMENTS

| | | |
|---|---|---|
| EP | 0838447 A1 | 4/1998 |
| WO | WO 95/21806 A | 8/1995 |

OTHER PUBLICATIONS

Chiappe et al., Green Chemistry (2006), 8 p. 277-281; published on web: Sep. 28, 2005.*
Wilkes, "Friedel-Crafts Reactions in Chloroaluminate Molten Salts," *Molten Salt Chemistry: An Introduction and Selected Applications* 405 (Mamantov and Marassi Eds. 1987).

Nelson, "Are Ionic Liquids Green Solvents?" 818 *ACS Symposium Series* 30-41 (American Chemical Society 2002).
Davis et al., "Synthesis and Purification of Ionic Liquids," *Ionic Liquids in Synthesis* 7 (Wasserschied & Welton Eds. 2003).
Anthony et al., "Physicochemical Properties of Ionic Liquids," *Ionic Liquids in Synthesis* 41 (Wasserschied & Welton Eds. 2003).
Earle et al, "Organic Synthesis," *Ionic Liquids in Synthesis* 174 (Wasserschied & Welton Eds. 2003).
Drake et al., "Structural Effects on the Physical Properties of Ionic Liquids," *Air Force Research Laboratory Report No.* AFRL-PR-ED-VG-2003-122 (May 2003).
"BASIL™—First Commercial Process Using Ionic Liquids" *Chemicals Research and Engineering* http://www.corporate.basf.com/en/innovationen/labors/chemikalien, 2004.
Boswell, "Technology Watch: Ionic Liquids Offer New Solutions" *Chemical Market Reporter* FR14-16 (Jan. 2004).
Freemantle, "Designer Liquids in Polymer Systems" *Chemical and Engineering News* 26-29 (May 2004).
Parkinson, "Ionic Liquids Make and Environmental Splash," 100 *Chemical Engineering Process* 7 (Sep. 2004).
Holbrey, "Industrial Applications of Ionic Liquids," *Chemistry Today* 35 (Jun. 2004).
Ross, James et al. "*Friedel-Crafts Acylation Reactions Using Metal Triflates in Ionic Liquid*" Green Chemistry. Appearing in Green Chemistry, The Royal Society of Chemistry, at pp. 129-133 (2002) [XP-002434266].
Chiappe, Cinzia et al., "*Direct nono-N-alkylation of Amines in Ionic Liquids: Chemoselectivity and Reactivity*" Green Chemistry. Appearing in The Royal Society of Chemistry at pp. 193-197 (2003) [XP-002434266].
Boon, Jeffrey A. et al., "*Friedel-Crafts Reactions in Ambient Temperature Molten Salts*" appearing in The American Chemical Society at pp. 480-483. (1986) [XP-000943014.

* cited by examiner

*Primary Examiner*—Brian J Davis
(74) *Attorney, Agent, or Firm*—Jaimes Sher

(57) ABSTRACT

A process for ring-alkylating aniline or an aniline derivative in which aniline or an aniline derivative is reacted with an alkylating agent in the presence of an ionic liquid which includes a Lewis acid and a quaternary cation, to produce a ring-alkylated alkylaniline or a ring-alkylated aniline derivative. The use of an ionic liquid permits convenient separation of the alkylated reaction product from the reactants.

24 Claims, No Drawings

RING ALKYLATION OF ANILINE OR AN ANILINE DERIVATIVE USING IONIC LIQUID CATALYSTS

BACKGROUND OF THE INVENTION

The present invention relates to the ring alkylation of aniline or an alkylated aniline derivative.

Aniline is an important building block for rubber chemicals (such as diphenylamine, 4-aminodiphenylamine, mercaptobenzothiazole disulfide), dyes, polyanilines and petroleum additives, and crop chemicals. In applications where good hydrocarbon solubility of the compound is important, it is necessary to introduce hydrocarbon chains onto aniline or alkylated anilines to improve solubility.

The prior art has sought to improve the ring alkylation of aromatic amines such as aniline. For example, U.S. Pat. Nos. 4,740,620 and 4,876,377 disclose selective ring alkylation of aromatic amines to an ortho-alkylated product, using an acidic crystalline molecular sieve and partially dealuminated zeolites, respectively. U.S. Pat. No. 5,081,302 discloses the selective ring alkylation of aniline in the presence of zeolite catalysts to para-alkylaniline.

An ionic liquid consists of inorganic and/or organic cations and anions, and typically has a very low vapor pressure, a wide liquid temperature range, and is non-flammable. Ionic liquids can act as a catalyst and/or solvent, and have been studied for utility as solvents, electrolytes, in separations and in fluid applications such as lubricants. See Holbrey, "Industrial Applications of Ionic Liquids," *Chemistry Today* 35 (June 2004); Parkinson, "Ionic Liquids Make an Environmental Splash," 100 *Chemical Engineering Progress* 7 (September 2004); and Drake et al., "Structural Effects on the Physical Properties of Ionic Liquids," *Air Force Research Laboratory Report* No. AFRL-PR-ED-VG-2003-12 (May 2003).

The use of ionic liquids in Friedel-Crafts alkylation has been discussed in Wilkes, "Friedel-Crafts Reactions in Chloroaluminate Molten Salts," *Molten Salt Chemistry: An Introduction and Selected Applications* 405 (Mamantov and Marassi Eds. 1987) and Earle et al., "Organic Synthesis," *Ionic Liquids in Synthesis* 174 (Wasserschied & Welton Eds. 2003). However, neither study is directed to ring alkylation of aniline or an aniline derivative.

An object of the invention is to provide an improved synthesis for ring alkylation of aniline or an aniline derivative.

A feature of the invention is the use of an ionic liquid as a solvent and catalyst for the ring alkylation of aniline or an aniline derivative.

An advantage of the invention is that use of an ionic liquid typically permits convenient separation of alkylated aniline(s) and alkylated aniline derivative(s) from the reaction mixture.

BRIEF SUMMARY OF THE INVENTION

In one aspect, the present invention relates to a process for ring-alkylating aniline or an aniline derivative, comprising reacting aniline or an aniline derivative with an alkylating agent in the presence of an ionic liquid comprising a Lewis acid and a quaternary cation, to produce an alkylaniline or an alkylated aniline derivative.

DETAILED DESCRIPTION OF THE PREFERRED EMBODIMENTS

As summarized above, the present invention relates to the ring alkylation of aniline or an aniline derivative in the presence of an ionic liquid. By "aniline derivative" it is meant aniline substituted with at least one $C_{1-18}$ alkyl substituent, either on the aromatic ring or the nitrogen atom. Illustrative ring alkylated aniline derivatives include ortho, para, meta-methylanilines, ortho, para, meta-ethylanilines, and ortho, para, meta-butylanilines and ortho, para, meta-octyldecylanilines. Illustrative N-alkylated aniline derivatives include N-methylaniline, N,N-dimethylaniline and N,N-diethylaniline.

The alkylating agent may be a substituted or unsubstituted linear, branched or cyclic olefin or an arylalkene. Suitable linear olefins include 1-hexene, 1-nonene, 1-decene and 1-dodecene. Suitable branched olefins include propylene trimer (nonenes), propylene tetramer (dodecenes), propylene pentamer and diisobutylene. Suitable cyclic olefins include cyclohexene, cyclopentene and cyclooctene. Suitable arylalkylenes include styrene, methyl styrene, 3-phenylpropene and 2-phenyl-2-butene.

The ionic liquid may be composed entirely of anions and cations, and may conveniently be prepared by mixing together a Lewis acid and an alkyl quaternary metal salt, preferably under heat.

The Lewis acid may be a metal halide, an alkyl halide, an alkylaryl halide or an alkyl sulfonate ester. Suitable Lewis acid metal halides include aluminum chloride, aluminum bromide, indium trichloride, gallium trichloride, niobium pentachloride, tantalum pentachloride, titanium tetrachloride, boron trifluoride, boron trifluoride etherate, boron trichloride, ferric chloride, and zirconium chloride. Illustrative alkyl halides include methyl chloride, methyl bromide, methyl iodide, ethyl chloride, ethyl bromide, ethyl iodide, n-propyl chloride, n-propyl bromide, n-propyl iodide, isopropyl chloride, isopropyl bromide, isopropyl iodide, n-butyl chloride, n-butyl bromide, n-butyl iodide, isobutyl chloride, isobutyl bromide, isobutyl iodide, tert-butyl chloride, tert-butyl bromide, tert-butyl iodide, n-pentyl chloride, n-pentyl bromide, n-pentyl iodide, neopentyl bromide, neopentyl chloride, neopentyl iodide, octyl chloride, octyl bromide and octyl iodide. Illustrative alkylaryl halides include benzyl bromide, benzyl chloride, benzyl iodide, α-phenylethyl chloride, α-phenylethyl bromide, α-phenylethyl iodide, β-phenylethyl chloride, β-phenylethyl bromide and β-phenylethyl iodide. Suitable alkyl sulfonate esters include alkyl tosylates, alkyl mesylates and alkyl triflates.

The alkyl quaternary metal salt may be a quaternary ammonium salt, an alkylphosphonium salt, an alkylimidazolium salt, an alkyltriazolium salt and an alkylpyridinium salt. Suitable quaternary ammonium salts may be based on cations selected from the group consisting of benzyltrimethylammonium, butyltrimethylammmonium, methyltriethylammonnium, ethyltrimethylammonium, tetra-n-butylammonium, n-hexyl-trimethylammonium, n-heptyl-trimethylammonium, n-octyl-trimethylammonium, n-hexyl-triethylammonium, n-heptyl-triethylammonium, n-octyl-triethylammonium, n-hexyl-tri-n-butylammonium, n-heptyl-tri-n-butylammonium, n-octyl-tri-n-butylammonium, tris-(n-propyl)-undecylammonium, tetra-n-pentylammonium, N-decyl-n-octyl-dimethylammonium and N-tetradecyl-triethylammonium.

Suitable quaternary phosphonium salts may be based on cations selected from the group consisting of benzyltrimethylphosphonium, butyltrimethylphosphonium, methyltriethylphosphonium, ethyltrimethylphosphonium, tetra-n-butylphosphonium, n-hexyl-trimethylphosphonium, n-heptyl-trimethylphosphonium, n-octyl-trimethylphosphonium, n-hexyl-triethylphosphonium, n-heptyl-triethylphosphonium, n-octyl-triethylphosphonium, n-hexyl-tri-n-butylphosphonium, n-heptyl-tri-n-butylphosphonium, n-octyl-tri-n-butylphosphonium, tris-(n-propyl)-undecylphosphonium, tetra-n-pentylphosphonium, N-decyl-n-octyl-dimethylphosphonium and N-tetradecyl-triethylphosphonium.

Suitable alkylimidazolium salts may be based on cations selected from the group consisting of 1-methyl-3-methyl-imidazolium, 3-butyl-1-methyl-imidazolium, 1-ethyl-3-methyl-imidazolium, 1-butyl-3-methylimidazolium, 1-dodecyl-5-methylimidazolium, 1-(2,2,2-trifluoroethyl)-3-methylimidazolium, 1-(ethoxymethyl)-3-methylimidazolium, 3-ethyl-1-ethylimidazolium, 3-ethyl-1-butyl-imidazolium, 1-ethyl-2,3-dimethyl-imidazolium, 1,2-diethyl-3-methylimidazolium, 1-ethyl-3,5-dimethyl-imidazolium and 1,3-diethyl-5-methylimidazolium.

Suitable alkyltriazonium salts may be based on cations selected from the group consisting of 1-(3',3',3'-trifluoro-n-propyl)-3-n-butyl-1,2,4-triazolium, 1-(2'-fluoroethyl)-3-n-heptyl-1,2,4-triazolium, 1-(2'-fluoroethyl)-3-n-decyl-1,2,4-triazolium, 1-(1H,1H,2H,2H-perfluoro-n-hexyl-triazolium, 1-n-propyl-4-amino-1,2,4-triazolium, 1-n-butyl-4-amino-1,2,4-triazolium and 1-n-hexyl-4-amino-1,2,4-triazolium.

In a preferred embodiment, the ionic liquid is formed in situ prior to addition of the alkylating agent. The Lewis acid, alkyl quaternary metal salt and aniline or an aniline derivative may be added to a suitable reaction vessel, preferably under a dry, inert atmosphere and with heating to a temperature up to 250° C., and stirred, for example at 200 to 300 rpm, until an ionic liquid phase and an organic phase are formed. The inert atmosphere serves to protect the ionic liquid from oxidation and is preferably selected from the group consisting of argon, helium and nitrogen. The inert atmosphere should also be dry to avoid decomposition of the ionic liquid.

The alkylating agent may be added to the reaction vessel once the ionic liquid has been formed, either all at once or by multiple partial additions. Preferably, an excess of the alkylating agent is employed. For example, from 1.1 to 5.0 equiv. of olefin/mole aniline may be used, together with 10 to 50% mole % of the Lewis acid relative to the aniline, and an amount of the ionic liquid forming compound such that the mole fraction of Lewis acid is at least 0.60 to 0.90.

The alkylation reaction may preferably be performed at a temperature of from 50 to 250° C., still more preferably at a temperature of 80 to 200° C., over a time period of from 1 to 48 hours, still more preferably 12 to 30 hours.

The regioisomer produced by the alkylation reaction appears dependent on the choice of alkylating agent. For example, the use of alpha olefins (such as 1-decene) results in alkylation ortho to the nitrogen. Conversely, the use of branched olefins (such as propylene trimer) results in alkylation para to the nitrogen.

The alkylation reaction may also produce a mixture of mono and di-alkylated anilines. The reaction products may be separated from the reactants by conventional separation techniques and apparatus well known to one of ordinary skill in the art, such as, for example, a separatory funnel. Acidic impurities, if present in the product, may be removed by successive water and base washes. Similarly, the isolated reaction mixture may be separated into its component compounds using conventional separation techniques and apparatus well known to those of ordinary skill in the art, such as, for example, high-pressure liquid chromatography.

EXAMPLES

The following Examples illustrate the practice and advantages of the invention in greater detail with respect to individual species thereof. The details of the examples are illustrative only, and are not to be used to constrict the scope of the claims.

Example 1

Alkylation of Aniline Using 1-Decene, Aluminum Chloride and 3-butyl-1-methylimidiazolium chloride A 1-L, 4-necked round bottomed flask equipped with a mantle, temperature controller, a water cooled reflux condenser topped with inlet for nitrogen positive pressure, mechanical stirrer and a thermocouple was charged under nitrogen positive pressure with aniline (46.52 g, 0.50 mole), 1-decene (245.54 g, 1.75 mole, 3.5 equiv. relative to aniline), aluminum chloride (33.38 g, 0.25 mole, 50 mole % relative to aniline) and finally 3-butyl-1-methylimidiazolium chloride (BMIM chloride, 10. 0.0625 mole, 12.5 mole % relative to aniline). Stirring was started at ca. 200-300 rpm and the mixture warmed initially to 100° C., then to 160° C. and finally 180° C. The 1-decene underwent mild reflux at this temperature. Heating continued at 167-180° C. for a total of 23.4 hr.

The reaction mixture was allowed to cool back to room temperature and diluted with 400 mL n-heptane. The reaction products separated into two phases, with the upper phase having a dark brown color. The upper and lower phases were separated i n a separatory funnel, and the lower phase discarded. An exotherm occurred when the dark brown upper phase was treated with 500 mL water. The organic phase was washed with an additional 500 mL water, then 500 mL aq. ammonia (400 mL water plus 100 mL conc. aq. ammonia), and then dried over anhydrous sodium sulfate. The drying agent was removed by suction filtration and the filtrate stripped in vacuo (95° C. water bath, 6 mm final vacuum) to afford a reddish liquid, wt. 106.46 g. This was shown by GC to be a 25:75 mixture of mono/didecylated anilines. IR analysis indicated the position of alkylation to be ortho. Yield was 57% based on the GC analysis.

Example 2

Alkylation of Aniline Using Nonenes, Aluminum Chloride and Methyltributylammonium Chloride An apparatus similar to that described in Example 1 was charged with, in succession, aniline, nonenes and aluminum chloride under nitrogen. Stirring at 200-300 rpm was started and then solid methyltributylammonium chloride was added. Then heating to 160° C. was started. Reflux started at a pot temperature of 137.5° C. and increased steadily as the aniline was alkylated. Heating between 137-160° C. continued for 28.2 hr before the reaction mixture was allowed to cool to room temperature.

The reaction mixture was diluted with 300 mL n-heptane and 200 mL methylene chloride and two phases separated. No reaction resulted when the heptane phase was washed with 500 mL water. The cautious addition of 500 mL water to the methylene chloride lower phase resulted in a strong reaction, indicating this phase contained the catalyst. The heptane phase was added to the methylene chloride phase after the reaction, and then the layers shaken and re-separated. The heptane phase was washed with an additional 500 mL water, and then 500 mL aq. ammonia (400 mL water plus 100 mL conc. aq. ammonia) prior to being dried over anhydrous sodium sulfate.

The drying agent was removed by suction filtration and the filtrate condensed in vacuo (rotary evaporator, 95° C. bath, 3 mm final vacuum) to afford 70.09 g of reddish-orange oil. This was shown by GC to be mainly monon-onylaniline, yield 31.9%. IR analysis indicated the position of alkylation was para to the nitrogen atom.

Example 3

Alkylation of Aniline Using Dodecenes, Aluminum Chloride and Methyltributylammonium Chloride An apparatus similar to that described in Example 1 was charged with aniline, dodecenes under nitrogen positive pressure, followed by aluminum chloride and then slow stirring started. There was an exotherm up to 46° C. upon stirring and then methyltributylammonium chloride was added. The reaction mixture was heated to 160° C. and maintained at this temperature for 27.8 hr. The reaction mixture was then allowed to cool to room temperature and diluted with 300 mL n-heptane-200 mL methylene chloride.

The reaction mixture separated into a large volume upper phase and a dark red-orange lower phase. The upper layer was washed with 2×500 mL water, 500 mL aq. ammonia (400 mL water/100 mL conc. aq. ammonia) and then dried over anhydrous sodium sulfate.

The sodium sulfate was removed by suction filtration and the filtrate stripped on a rotary evaporator in vacuo (5 mm final vacuum, 95° C. water bath). The residue was a reddish-orange oil, wt. 136.96 g. This was shown to be monodode-cylaniline by GC. IR analysis indicated the position of alkylation was mainly para.

The inventors currently believe the ionic liquid may be recycled for use in subsequent alkylations by simple phase separation in which the hydrocarbon-soluble reaction product(s) is/are decanted, and thus separated from, the denser ionic liquid phase. The ionic liquid may then be used to catalyze another alkylation reaction by itself, or in combination with fresh catalyst.

We claim:

1. A process for ring-alkylating aniline or an aniline derivative, comprising reacting aniline or an aniline derivative with an alkylating agent in the presence of an ionic liquid comprising a Lewis acid and a quaternary cation, to produce a ring-alkylated alkylaniline or a ring-alkylated aniline derivative.

2. The process of claim 1, wherein aniline is reacted with said alkylating agent.

3. The process of claim 1, wherein said aniline derivative has at least one alkyl substituent bonded to the ring.

4. The process of claim 1, wherein said aniline derivative has at least one alkyl substituent bonded to the nitrogen atom.

5. The process of claim 1, wherein said alkylating agent is a substituted or unsubstituted linear, branched or cyclic olefin or an arylalkene.

6. The process of claim 5, wherein said olefin is a linear olefin selected from the group consisting of 1-hexene, 1-nonene, 1-decene and 1-dodecene.

7. The process of claim 5, wherein said olefin is a branched olefin selected from the group consisting of propylene trimer, propylene tetramer, propylene pentamer and diisobutylene.

8. The process of claim 5, wherein said olefin is a cyclic olefin selected from the group consisting of cyclohexene, cyclopentene and cyclooctene.

9. The process of claim 5, wherein said olefin is an arylalkene selected from the group consisting of styrene, methyl styrene, 3-phenylpropene and 2-phenyl-2-butene.

10. The process of claim 1, wherein said Lewis acid is a metal halide selected from the group consisting of aluminum chloride, aluminum bromide, indium trichloride, gallium trichloride, niobium pentachloride, tantalum pentachloride, titanium tetrachloride, boron trifluoride, boron trifluoride etherate, boron trichloride, feffic chloride, and zirconium chloride.

11. The process of claim 1, wherein said Lewis acid is an alkyl halide selected from the group consisting of methyl chloride, methyl bromide, methyl iodide, ethyl chloride, ethyl bromide, ethyl iodide, n-propyl chloride, n-propyl bromide, n-propyl iodide, isopropyl chloride, isopropyl bromide, isopropyl iodide, n-butyl chloride, n-butyl bromide, n-butyl iodide, isobutyl chloride, isobutyl bromide, isobutyl iodide, tert-butyl chloride, tert-butyl bromide, tert-butyl iodide, n-pentyl chloride, n-pentyl bromide, n-pentyl iodide, neopentyl bromide, neopentyl chloride, neopentyl iodide, octyl chloride, octyl bromide and octyl iodide.

12. The process of claim 1, wherein said Lewis acid is an alkylaryl halide selected from the group consisting of benzyl bromide, benzyl chloride, benzyl iodide, a-phenylethyl chloride, α-phenylethyl bromide, α-phenylethyl iodide, β-phenylethyl chloride, β-phenylethyl bromide and β-phenylethyl iodide.

13. The process of claim 1, wherein said Lewis acid is an alkyl sulfonate ester.

14. The process of claim 1, wherein said quaternary cation is selected from a quaternary ammonium cation, an alkylphosphonium cation, an alkylimidazolium cation, an alkyltriazolium cation and an alkylpyridinium cation.

15. The process of claim 14, wherein said quaternary ammonium cation is a member selected from the group consisting of benzyltrimethylammonium, butyltrimethylammonium, methyltriethylammonnium, ethyltrimethylammonium, tetra-n-butylammonium, n-hexyl-trimethyla-monium, n-heptyl-trimethylammonium, n-octyl-trimethylammonium, n-hexyl-triethylamonium, n-heptyl-triethylammonium, n-octyl-triethylammonium, n-hexyl-tri-n-butylamonium, n-heptyl-tri-n-butylammonium, n-octyl-tri-n-butylammonium, tris-(n-propyl)-undecylammonium, tetra-n-pentylammonium, n-decyl-n-octyl-dimethylammo-nium and n-tetradecyl-triethylammonium.

16. The process of claim 14, wherein said alkylimidazolium cation is a member selected from the group consisting of 1-methyl-3-methyl-imidazolium, 1-ethyl-3-methyl-imidazolium, 1-butyl-3-methylimidazolium, 1-dodecyl-5-methylimidazolium, 1-(2,2,2-trifluoroethyl)-3-methylimidazolium, 1-(ethoxymethyl)-3-methylimidazolium, 3-ethyl-1-ethylimidazolium, 3-ethyl-1-butyl-imidazolium, 1-ethyl-2,3-dimethyl-imidazolium, 1,2-diethyl-3-methylimidazolium, 1-ethyl-3,5-dimethyl-imidazolium and 1,3-diethyl-5-methylimidazolium.

17. The process of claim 14, wherein said alkyltriazolium cation is a member selected from the group consisting of 1-(3',3',3'-trifluoro-n-propyl)-3-n-butyl-1,2,4-triazolium, 1-(2'-fluoroethyl)-3-n-heptyl-1,2,4-triazolium, 1-(2'-fluoroethyl)-3-n-decyl-1,2,4-triazolium, 1-(1H,1H,2H,2H-perfluoro-n-hexyl)-3-n-butyl-1,2,4-triazolium, 1-n-propyl-4-amino-1,2,4-triazolium, 1-n-butyl-4-amino-1,2,4-triazolium and 1-n-hexyl-4-amino-1,2,4-triazolium.

18. The process of claim 1, wherein said ionic liquid is formed in situ prior to addition of said alkylating agent.

19. The process of claim 1, performed at a temperature of from 50 to 250° C. over a time period of from 1 to 48 hours.

20. The process of claim 1, performed under an inert atmosphere selected from the group consisting of argon, helium and nitrogen.

21. The process of claim 1, performed with stirring at a stirring speed of from 100 to 500 rpm.

22. A process for ring-alkylating aniline or an aniline derivative, comprising reacting aniline or an aniline derivative with an alkylating agent in the presence of an ionic liquid to produce a ring-alkylated alkylaniline or a ring-alkylated aniline derivative, wherein the mole ratio of said alkylating agent to said aniline or said aniline derivative is 1.1 or greater.

23. The process of claim 22, wherein the mole ratio of said alkylating agent to said aniline or said aniline derivative is 1.1 to 5.0.

24. The process of claim 22, wherein the ionic liquid comprises a Lewis acid and a quaternary cation.

* * * * *